United States Patent [19]
Tomiyama et al.

[11] Patent Number: 6,124,460
[45] Date of Patent: Sep. 26, 2000

[54] ISOQUINUCLIDINE DERIVATIVES, METHOD OF MANUFACTURING THE SAME AND THERAPEUTIC AGENTS FOR HYPERCHOLESTEROLEMIA CONTAINING THESE COMPOUNDS

[75] Inventors: Tsuyoshi Tomiyama; Akira Tomiyama; Takeyuki Imamaki, all of Sakaki-machi; Naoto Ueyama, Ueda; Motoharu Sonegawa, Nagano; Satoru Takeuchi, Sakaki-machi, all of Japan

[73] Assignee: Kotobuki Pharmaceutical Co. Ltd., Nagano-ken, Japan

[21] Appl. No.: 09/441,515

[22] Filed: Nov. 17, 1999

[30] Foreign Application Priority Data

Dec. 7, 1998 [JP] Japan ................................. 10-346768

[51] Int. Cl.[7] .................................................. C07D 453/06
[52] U.S. Cl. ............................................ 546/112; 546/183
[58] Field of Search ..................................... 546/112, 183; 514/299

[56] References Cited

U.S. PATENT DOCUMENTS 3,764,605  10/1973  Plumpe et al. .......................... 546/112

*Primary Examiner*—Bernard Dentz

[57] ABSTRACT

New therapeutic agents of isoquinuclidine derivatives are represented by the following formula or its hydrochloride salts.

(I)

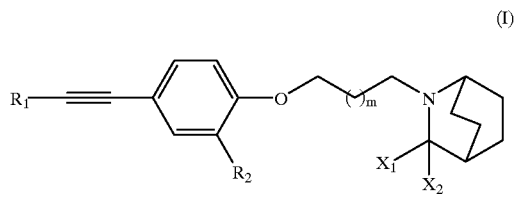

(wherein $R_1$ is hydrogen, carboxyl group, ethoxycarbonyl group, 4-(ethoxycarbonyl)phenyl group, 4-(carboxy)phenyl group, 2-(carboxy)-thiophene-5-yl group, quinoline-5-yl group, 4-(quinoline-5-yl)phenyl group or 4-(3-oxo-2-azabicyclo[2.2.2]octane-2-yl)-phenyl group; $R_2$ is hydrogen or allyl group; Both $X_1$ and $X_2$ are hydrogen and $X_1$ and $X_2$ may form an oxo group; m stands for an integer of 0 to 2.) These compounds, have excellent inhibitory activities against squalene synthase, and are useful as a treatment agent for hypercholesterolemia.

19 Claims, No Drawings

ISOQUINUCLIDINE DERIVATIVES, METHOD OF MANUFACTURING THE SAME AND THERAPEUTIC AGENTS FOR HYPERCHOLESTEROLEMIA CONTAINING THESE COMPOUNDS

BACKGROUND OF THE INVENTION

1. Field of the Invention

This invention relates to a novel isoquinuclidine derivative, a production method thereof, and a treatment agent for hypercholesterolemia containing the isoquinuclidines.

2. Description of the Prior Art

Recently, hyperlipidemic patients are increasing because the eating habits are changing to western style to take excess meats and the ingestion of excess fat. It has been shown that atherosclerosis is a complex, progressive and multifactorial vascular disease which is induced by narrowing and occlusion of arterial vessels, and its disease is accompanied with angina, hemorrhage, thrombosis, and cerebral and myocardial infarction. Hypercholesterolemia and hyperlipoproteinemia are considered as main risk factors in the progression of the disease. Furthermore it has been shown that there is a correlation between low-density lipoprotein-cholesterol (LDL-C) and incidence of coronary heart disease. Over 70% of cholesterol in the body is derived from de novo cholesterol biosynthesis, inhibition of which is currently the most effective clinical means of reducing plasma LDL-C levels. In the present, HMG-CoA reductase inhibitors which inhibit as transformation of mevalonic acid from 3-hydroxy-3-methylglutaryl coenzyme in cholesterol biosynthesis such as mevalostatin, have been used for the treatment of hypercholesterolemia but the HMG-CoA reductase inhibitors have a possibility that these compounds also inhibit a biosynthesis of nonsterol products (isoprenoid, dolicol and ubiquinone etc) derived from the farnesyl diphosphate. Therefore, it has been hoping to find an inhibitor that not suppress isoprenoids synthesis but inhibits squalene. (J. L. Goldstein, Nature, 343, 425 (1990), Chuen chan et al., J. Med. Chem., 39, 207 (1996))

Recently, the natural products which had an inhibitory activity toward cholesterol biosynthesis were discovered from several groups. (O. D. Hensen et al., Tetrahedron Lett., 34, 399 (1993), M. J. Dawson et al., J. Antibiot., 45, 639 (1992)) It was found that these natural products inhibit the squalene synthease (SQS) which catalyzed the two-step conversion from two molecules of farnesyl diphosphate (FPP), via presqualene diphosphate to squalene, which is the first biosynthetic step leading to sterols. Therefore, agents which inhibit this enzyme are considered as a more effective inhibitor of cholesterol biosynthesis, since biosynthesis of nonsteroidal products is not affected. Further, the SQS inhibitors of non-natural type were reported from several groups. (G. R. Brown et al., J. Med. Chem., 39, 2971 (1996), J. A. Brinkman et al., Bioorg. Med. Chem. Lett., 6, 2491 (1996)) But these natural and non-natural products have problems such as lack of stability or oral activity.

Problems to be Solved by the Invention

A primary object of the present invention is to find a new isoquinuclidine derivative having SQS inhibition and provide a treatment agent for hypercholesterolemia and a production method thereof.

SUMMARY OF THE INVENTION

The principal object of the present invention is the provision of compounds having SQS inhibition action.

Another object of the present invention is the provision of pharmaceutical compositions useful as antihypercholesterolemia agents.

Still another object of the present invention is the provision of new isoquinuclidine derivatives and a method for the manufacture thereof.

These and other objects of the invention will become apparent from the description that follows.

DETAILED DESCRIPTION OF THE INVENTION

The inventors have conducted intensive studies on compounds having SQS inhibition, and found that there are compounds in isoquinuclidine derivatives which have SQS inhibition, achieving the present invention.

In accordance with the present invention, there is provided a new isoquinuclidine derivative compound of general formula (1) or its salt capable of being used for medical treatment and a production method thereof.

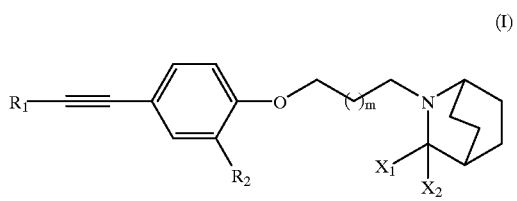

(I)

(wherein $R_1$ is hydrogen, carboxyl group, ethoxycarbonyl group, 4-(ethoxycarbonyl)phenyl group, 4-(carboxy)phenyl group, 2-(carboxy)-thiophene-5-yl group, quinoline-5-yl group, 4-(quinoline-5-yl)phenyl group or 4-(3-oxo-2-azabicyclo[2.2.2]octane-2-yl)phenyl group; $R_2$ is hydrogen or allyl group; Both $X_1$ and $X_2$ are hydrogen or $X_1$ and $X_2$ may form an oxo group; m stands for an integer of 0 to 2.)

The compounds related to the general formula (1) possesses a potent SQS inhibitor and they are regarded as therapeutically useful.

The compounds shown in the general formula (1) can be synthesized by the following method.

1. In the compounds shown in the general formula (1), the synthetic pathway of the compounds, wherein $R_1$ is hydrogen or carboxyl group or ethoxycarbonyl group and $R_2$ is hydrogen and both $X_1$ and $X_2$ are the same as mentioned above, are shown in both scheme 1 and scheme 2.

[Scheme 1]

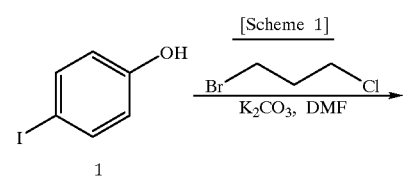

1

3
-continued

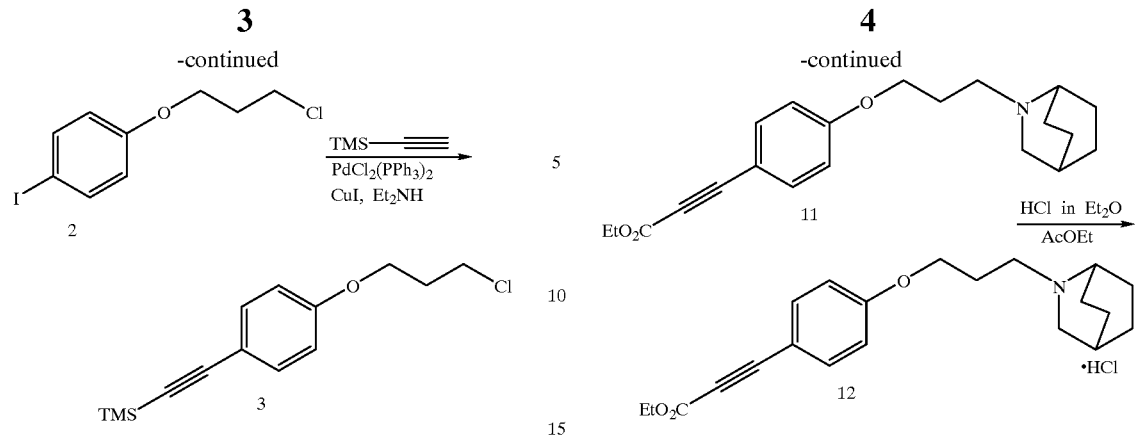

[Scheme 2]

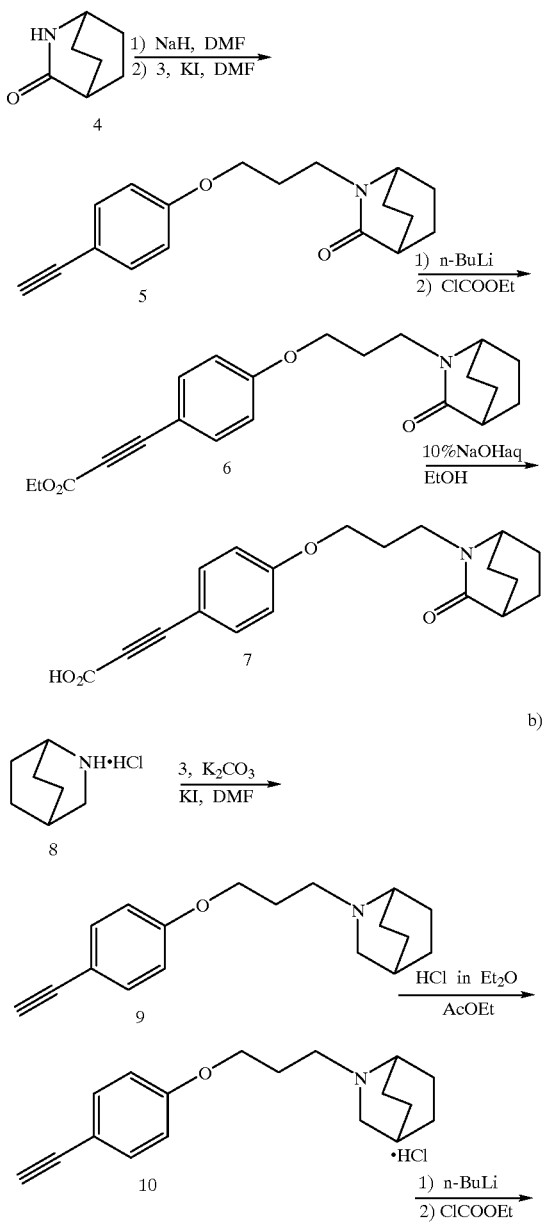

4
-continued

That is to say, in scheme 1, the reaction of 4-iodo-phenol (1) and 1-bromo-3-chloropropane is carried in the presence of potassium bicarbonate ($K_2CO_3$) in N,N-dimethylformamide (DMF) to yield 4-iodo-phenol derivative (2), then 4-iodo-phenol derivative (2) is reacted with trimethylsilyl (TMS)-acetylene in the presence of bis (triphenylphosphine)dichloro palladium (($Ph_3P)_2PdCl_2$) and copper iodide (CuI) using diethylamine as solvent to give TMS-ethynyl-phenyl ether derivative (3).

In the a) route at scheme 2,2-azabicyclo[2.2.2]octan-3-one(isoquinuclidine-3-one) (4) is treated with sodium hydride (NaH) in DMF, then it is reacted with the intermediate as above (3) in the presence of potassium iodide to yield 2-[3-(4-ethynylphenoxy)propane-1-yl]-2-azabicyclo [2.2.2]octane-3-one (compound 5). Further, compound 5 is treated with n-butyl lithium (n-BuLi), then it is reacted with ethyl chloroformate to obtain ethyl 4-[3-(3-oxo-2-azabicyclo[2.2.2]octan-2-yl)propoxy]phenylpropiolate (compound 6). Then 4-[3-(3-oxo-2-azabicyclo[2.2.2]octan-2-yl)propoxy]phenylpropiolic acid (compound 7) is provided by the hydrolysis of compound 6 using 10% sodium hydroxide in water solution (10% NaOHaq).

In the b) route of scheme 2,2-azabicyclo[2.2.2]octane hydrochloride (isoquinuclidine hydrochloride) (8) is reacted with TMS-ethynyl-phenyl ether derivative (3) in the presence of $K_2CO_3$ and potassium iodide (KI). The resulting 2-[3-(4-ethynylphenoxy)propane-1-yl]-2-azabicyclo[2.2.2] octane (9) is treated with ethyl ether solution in saturated hydrochloride gas (HCl gas in ether) to obtain 2-[3-(4-ethynylphenoxy)propane-1-yl]-2-azabicyclo[2.2.2]octane hydrochloride (compound 10). Further, this compound 10 is treated with n-BuLi, then it is reacted with ethyl chloroformate in tetrahydrofuran (THF) to give an ethyl 4-[3-(2-azabicyclo[2.2.2]octan-2-yl)propoxy]phenylpropiolate (11), then it is treated by the same method as mentioned above to provide an ethyl 4-[3-(2-azabicyclo[2.2.2]octan-2-yl) propoxy]phenylpropiolate hydrochloride (compound 12). In case of both $R_1$ and $R_2$ are hydrogen and m is 0 or 2 in the compounds of general formula (1), compound 13 (m=0) and compound 14 (m=2), it is prepared by the same method of scheme 1 and a) route of scheme 2 using either a 1,2-dibromoethane or a 1,4-dibromobutane in the place of a 1-bromo-3-chloropropane.

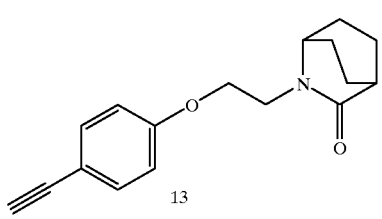

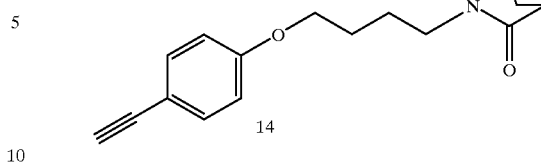

2. The compounds, wherein $R_1$ is 4-(ethoxycarbonyl)-phenyl group, 4-(carboxy)-phenyl group, 2-(carboxy)-thiophene-5-yl group, quinoline-5-yl group, 4-(quinoline-5-yl) phenyl group or 4-(isoquinuclidinone-2-yl)-phenyl group and $R_2$ is hydrogen and both $X_1$ and $X_2$ are the same as mentioned above as well as m is 1, are prepared by the method of scheme 3 using either compound 5 in a) route of scheme 2 or compound 9 in b) route of scheme 2.

[Scheme 3]

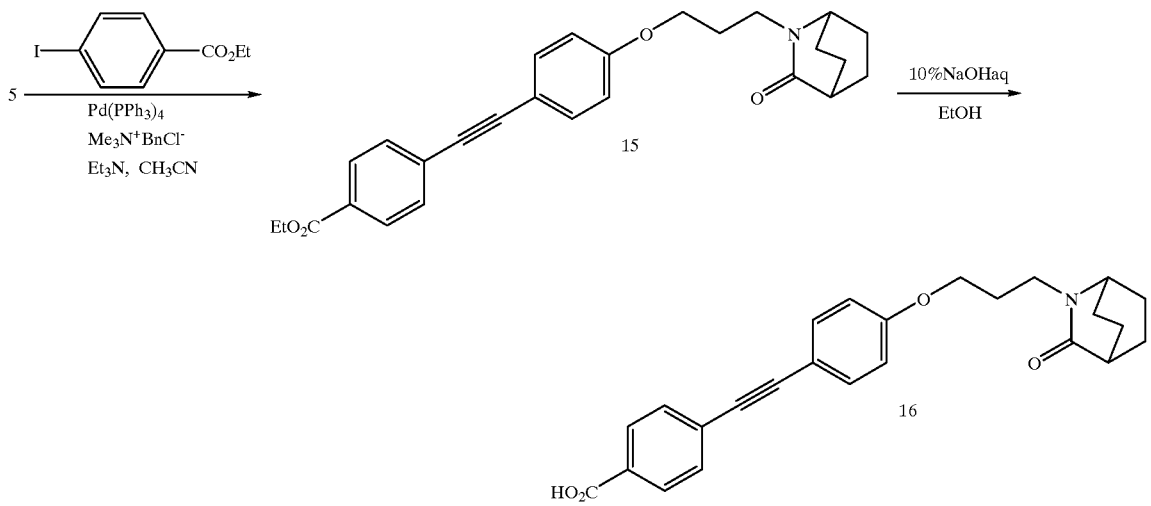

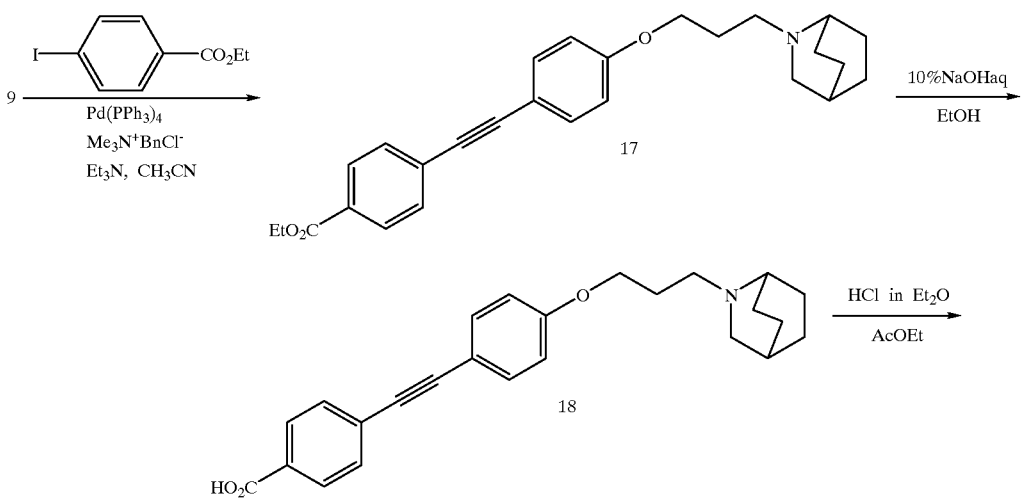

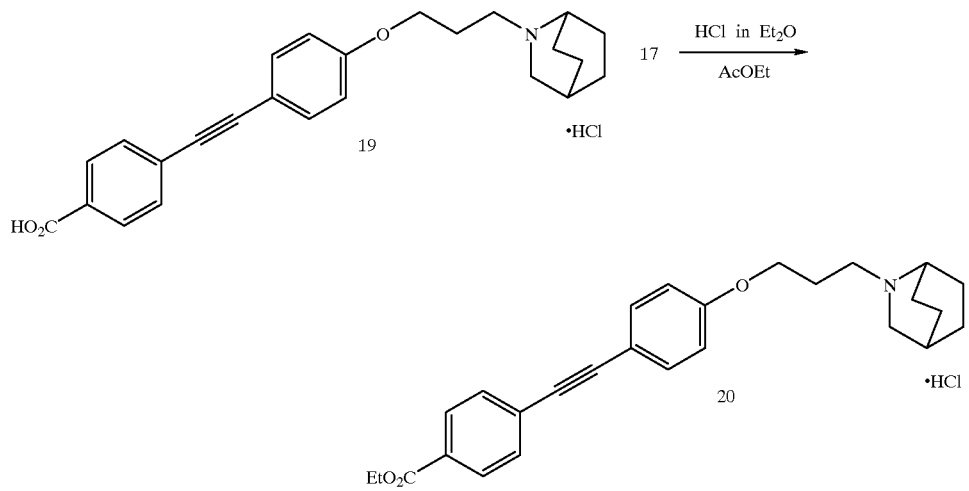

In the a) route of scheme 3, compound 5 is reacted with ethyl 4-iodo-benzoate in the presence of triethylamine (Et₃N), trimethyl-benzylammonium chloride (Me₃N (Bn) Cl) and tetrakistriphenylphosphine palladium (Pd(PPh₃)₄) to give ethyl 4-[4-[3-(3-oxo-2-azabicyclo[2.2.2]octan-2-yl) propoxy]phenylethynyl]-benzoate (compound 15), then 4-[4-[3-(3-oxo-2-azabicyclo[2.2.2]octan-2-yl)propoxy] phenylethynyl]-benzoic acid (compound 16 ) is provided by hydrolysis of compound 15.

In other, in the b) route of scheme 3, compound 17 and 18 are prepared from compound 9 in a similar manner as a) route of scheme 3, then it is treated with HCl gas in ether to give both 4-[4-[4-[3-(2-azabicyclo[2.2.2]octan-2-yl) propoxy]phenylethynyl]-benzoic acid hydrochloride (compound 19) and ethyl 4-[4-[3-(2-azabicyclo[2.2.2]octan-2-yl) propoxy]phenylethynyl]-benzoate hydrochloride (compound 20).

In the a) or b) route of scheme 3, the compounds which have the general formula ($R_1$–$X_4$), wherein $R_1$ is either 2-(carboxy)-thiophene-5-yl group, quinoline-5-yl group, 4-(quinoline -5-yl)phenyl group, 4-(isoquinuclidinone-2-yl)-phenyl group and $X_3$ is either halogen or triflate group (Tf), can be used as instead of ethyl 4-iodobenzoate.

The compounds, where are able to be prepared from the compounds having the general formula ($R_1$–$X_4$), are as follows.

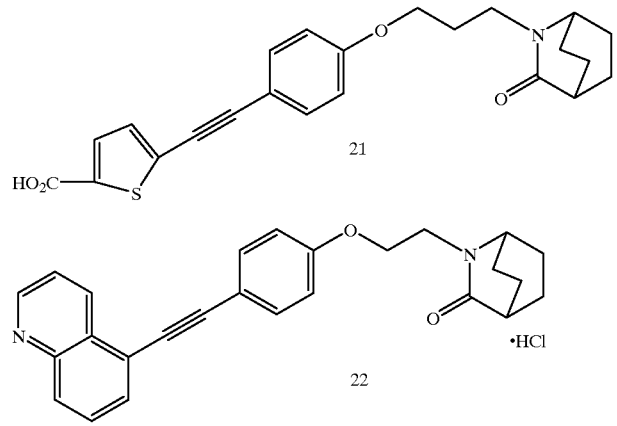

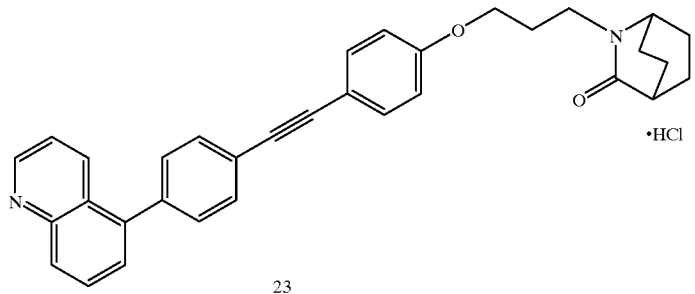
23
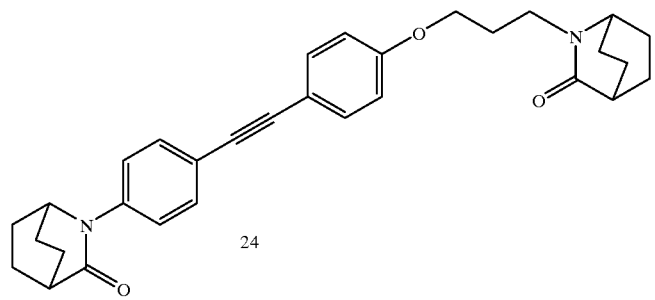
24
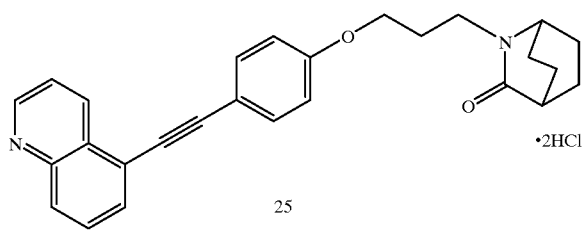
25
In the compounds having the general formula (R₁–X₄), the preparation of 4-(quinolin-5-yl)phenyl triflate and 4-(isoquinuclidin-2-yl)phenyl triflate are shown by a) or b) route of scheme 4.
[Scheme 4]
a)
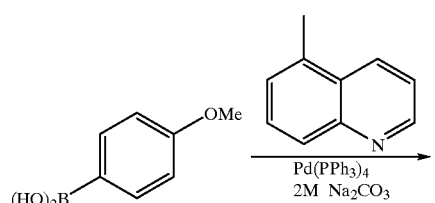
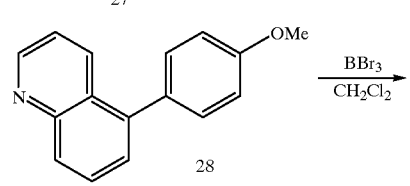
-continued
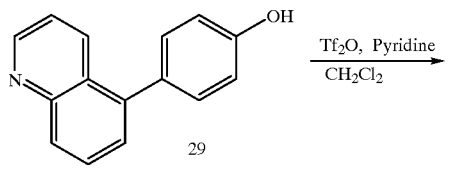
b)
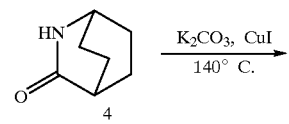

-continued

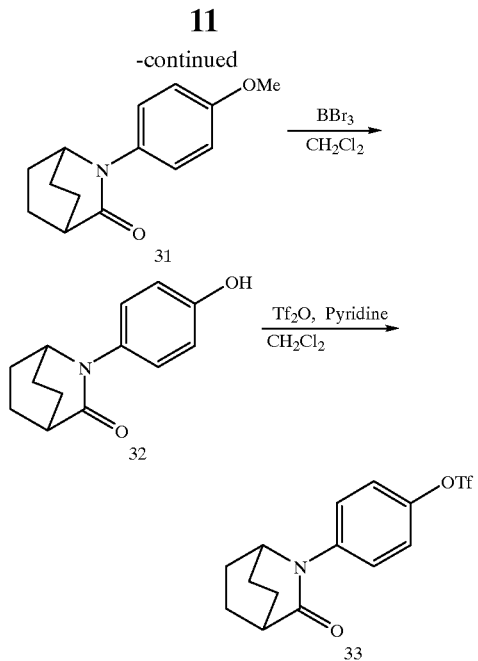

In the a) route of scheme 4, 4-methoxyphenylboronic acid (27), which is prepared from 4-iodoanisole (26), is reacted with 5-iodoaniline to provide anisole derivative (28). After anisole derivative (28) is treated with boron tribromide (BBr₃), it is reacted with trifloromethanesulfonic acid anhydride in the presence of pyridine to provide the triflate derivative (30).

In other, in the b) route of scheme 4, the Ullmann coupling of 4-iodoanisole (26) with isoquinuclidinone (4) yields 4-(isoquinuclidinon-2-yl)anisole (31), then triflate derivative (33) is prepared from compound 31 in such a manner as the a) route of scheme 4 and both ethyl 5-bromo-thiophen-2-carboxylate and 5-iodoquinoline is known.

3. The compounds, wherein $R_1$ is hydrogen and $R_2$ is allyl group and m is 1 and both $X_1$ and $X_2$ are the same as mentioned above, are prepared by the method of scheme 1, as well as a) route of scheme 2 using an intermediate (36) in the scheme 5.

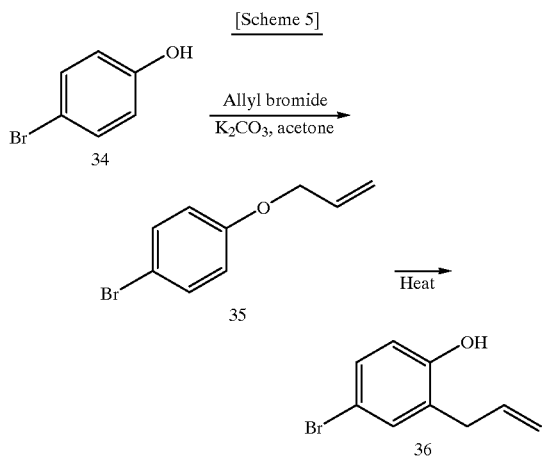

That is to say, 4-bromophenol (34) is reacted with allyl bromide in the presence of $K_2CO_3$ to give allyl ether derivative (35), then allyl ether derivative (35) is heated to yield 2-allyl-4-bromophenol (36).

The compounds which are prepared by the manner of scheme I and a) or b) route of scheme 2 using 2-allyl-4-bromophenol (36) are shown as follows.

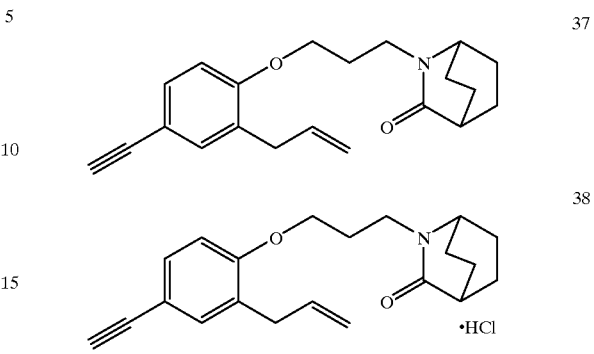

The compounds related to the general formula (1) are exemplified as follows. A number of the individual compounds in parentheses correspond to the number in synthetic pathway which were discussed above and in the following examples.

1. 2-[3-(4-ethynylphenoxy)propane-1-yl]-2-azabicyclo[2.2.2]octane-3-one (Compound 5)
2. Ethyl 4-[3-(3-oxo-2-azabicyclo[2.2.2]octan-2-yl)propoxy]phenylpropiolate (Compound 6)
3. 4-[3-(3-oxo-2-azabicyclo[2.2.2]octan-2-yl)propoxy]phenylpropiolic acid (Compound 7)
4. 2-[3-(4-ethynylphenoxy)propane-1-yl]-2-azabicyclo[2.2.2]octane hydrochloride (Compound 10)
5. Ethyl 4-[3-(2-azabicyclo[2.2.2]octan-2-yl) propoxy] phenylpropiolate hydrochloride (Compound 12)
6. 2-[2-(4-ethynylphenoxy)ethyl]-2-azabicyclo[2.2.2]octane-3-one (Compound 13)
7. 2-[4-(4-ethynylphenoxy)butane-1-yl ]-2-azabicyclo[2.2.2]octane-3one (Compound 14)
8. Ethyl 4-[4-[3-(3-oxo-2-azabicyclo[2.2.2]octan-2-yl)propoxy]phenylethynyl]-benzoate (Compound 15)
9. 4-[4-[3-(3-oxo-2-azabicyclo[2.2.2]octan-2-yl)propoxy]phenylethynyl]-benzoic acid (Compound 16)
10. 4-[4-[3-(2-azabicyclo[2.2.2]octan-2-yl)propoxy]phenylethynyl]-benzoic acid hydrochloride (Compound 19)
11. Ethyl 4-[4-[3-(2-azabicyclo[2.2.2]octan-2-yl)propoxy]phenylethynyl]-benzoate hydrochloride (Compound 20)
12. 5-[4-[3-(3-oxo-2-azabicyclo[2.2 2]octan-2-yl) propoxy] phenylethynyl]-thiophene-2-carboxylic acid (Compound 21)
13. 2-[3-[4-(quinolin-5-yl-ethynyl)phenoxy]propan-1-yl]-2-azabicyclo[2.2.2]-octan-3-one hydrochloride (Compound 22)
14. 2-[3-[4-[4-(quinolin-5-yl)phenylethynyl]phenoxy]propan-1-yl]-2-azabicyclo[2.2.2]octan-3-one hydrochloride (Compound 23)
15. 2-[3-[4-[4-(3-oxo-2-azabicyclo[2.2.2]octan-2-yl)phenylethynyl]phenoxy]propan-1-yl]-2-azabicyclo[2.2.2]octan-3-one (Compound 24)
16. 2-[3-[4-(quinolin-5-yl-ethynyl)phenoxy]propan-1-yl]-2-azabicyclo[2.2.2]-octane dihydrochloride (Compound 25)
17. 2-[3-[(2-allyl-4-ethynyl)phenoxy]propane-1-yl]-2-azabicyclo[2.2.2]oct-3-one (Compound 37)
18. 2-[3-[(2-allyl-4-ethynyl)phenoxy]propane-1-yl]-2-azabicyclo[2.2.2]octane hydrochloride (Compound 38)

Pharmacological Experiment

The method of pharmacological experiments and pharmacological data are shown as follows.

1. Assay of Squalene Synthase in Rat Liver Microsomes

Squalene synthase assay was performed in accordance with the method described by Mc Taggart et al. (Biochem. Pharmacol., 51, 1477 (1996)).

That is to say, microsomes were prepared from male Sprague-Dawley rat (weight range 250–300 g) by homogenising in 50 mM phosphate buffer, pH 7.4, 5.0 mM $MgCl_2$, 1.0 mM EDTA, and 1.0 mM dithiothreitol using a polytron (Kinetica, Sweden). The homogenates were centrifuged at 10,000 g for 20 min at 4° C., and, after spinning the supernatants were poured into the tube through cotton gauze. Microsomes were then isolated from the supernatant by centrifugation at 178,000 g for 90 min at 4° C. Microsomes were then resuspended in homogenisation buffer and stored in aliquots at −80° C. until use. For in vitro studies, the compounds were dissolved in DMSO. The squalene synthase reaction system in a volume of 100 µl contained 50 mM phosphate buffer, pH 7.4, 5.0 mM $MgCl_2$, 10 mM KF, 0.5 mM NADPH, 50 mM ascorbic acid, 20U /ml ascorbate oxidase, 2.5 µM farnesyl-pyrophosphate (FPP) and microsomes, 40 µg/ml.

The compounds (in 1 µl DMSO), microsomes (in 10 µl buffer) and other reagent (34 µl) were pre-incubated for 5 min at 37° C. The reactions were started by the addition of 5 µl of an aqueous solution of FPP containing about 0.1 µCi of [H] FPP; incubations were at 37° C. for 30 min. The reactions were then stopped by the addition of 50 µl of 20% KOH in 50% ethanol. The reaction mixture was extracted with 0.25 ml petroleum ether for 10 min and counts in the petroleum ether fraction (0.2 ml) were determined. The $IC_{50}$ values were calculated.

2. Assay of Sterol Biosynthesis in Rats

Sterol biosynthesis assay was performed according to the method described by Brown et al. (J. Med. Chem.,38, 4157 (1995)).

That is to say, female Sprague-Dawley rats (80–100 g) housed in reversed lighting conditions for one week before use. Compounds were dosed by oral gavage suspended in 10% DMSO in 0. 1% HPMC with control animals receiving vehicle alone. After 1 hr, rats were injected intraperitoneally with [H] mevalonolactone (2.5 µCi) in saline (0.25 ml). After a further 1 hr, rats were sacrificed, and a liver section (ca. 1 g) was removed. Livers were saponified with 3.3% KOH in ethanol at 70° C. for 2 hrs. The mixture was diluted with an equal volume water and extracted twice with petroleum ether (2.5ml). The petroleum ether was evaporated and counts in the residue were determined. Radioactivity was corrected for weight of liver. The results were expressed as the percentage inhibition against the vehicle-treated controls, and the $IC_{50}$ values were calculated.

The pharmacological data shown as follows.

TABLE 1

| Compound No. | Inhibition of SQS $IC_{50}$ (M) | Inhibition of cholesterol biosynthesis ($ED_{50}$(mg/kg, p.o.)) or % of inhibition[b] |
|---|---|---|
| 5 | $1.1 \times 10^{-8}$ | 13.4 |
| 6 | $3.1 \times 10^{-6}$ | N.T.[c] |
| 7 | $4.9 \times 10^{-7}$ | N.T. |
| 10 | $1.9 \times 10^{-8}$ | 48.6% (30 mg/kg p.o.) |
| 12 | $6.4 \times 10^{-8}$ | N.T. |
| 13 | N.E. ($10^{-5}$M)[a] | 30.3% (30 mg/kg p.o.) |
| 14 | $4.9 \times 10^{-7}$ | N.T. |
| 15 | $4.1 \times 10^{-7}$ | N.T. |
| 16 | $2.3 \times 10^{-8}$ | N.E. (30 mg/kg p.o.) |
| 19 | $3.9 \times 10^{-8}$ | N.E. (30 mg/kg p.o.) |
| 20 | $6.9 \times 10^{-7}$ | N.T. |
| 21 | $5.6 \times 10^{-8}$ | N.T. |
| 22 | $1.5 \times 10^{-8}$ | 25.1% (30 mg/kg p.o.) |
| 23 | $6.9 \times 10^{-8}$ | 46.7% (30 mg/kg p.o.) |
| 24 | $5.6 \times 10^{-5}$ | N.T. |
| 25 | $3.1 \times 10^{-8}$ | N.T. |
| 37 | N.E. ($10^{-5}$M) | N.T. |
| 38 | $1.1 \times 10^{-8}$ | 50.4% (30 mg/kg p.o.) |

[a]N.E.; no effect at a dose in the parentheses
[b]The values for % of inhibition indicate at a dose in the parentheses.
[c]N.T.; not tested

EXAMPLE

Example 1

2-[3-(4-Ethynylphenoxy)propane-1-yl]-2-azabicyclo [2.2.2]octan-3-one (compound 5) and 2-[3-(4-Ethynylphenoxy)propane-1-yl]-2-azabicyclo[2.2.2] octane hydrochloride (compound 10)

(a) TMS-ethynyl phenyl ether derivative (3)

To a solution of 4-iodophenol (3.0 g) in DMF (50 ml), 1-bromo-3-chloropropane (1.62 ml) and $K_2CO_3$ (2.83 g) were added. The reaction mixture was stirred at room temperature for 20 hrs, and DMF was distilled under reduced pressure. The residue was poured into ice-water and ethyl acetate. The resulting solution was extracted with ethyl acetate and the organic layer was washed with satd. $NH_4Cl$ aq, water and brine. The organic layer was dried ($Na_2SO_4$), filtered, and concentrated in vacuo. The residue was purified by column chromatography on silica gel and eluted with n-hexane-ethyl acetate (50:1). 3-chloro-1-(4-iodophenoxy) propane(2) was obtained as a colorless oil (3.15 g).

MASS (m/e): 296 (M$^+$), 260, 233, 220, 203, 134, 76 (BP)

IR (cm$^{-1}$, neat): 2926, 1584, 1482, 1470, 1389, 1281, 1239, 1173, 1032, 999, 945, 816, 657, 624

$^1$H-NMR (400 MHz, CDCl$_3$, ppm) d: 2.23 (2H, m), 3.73 (2H, t, J=6.0 Hz), 4.08 (2H, t, J=6.0 Hz), 6.68 (2H, d, J=9.2 Hz), 7.55 (2H, d, J=8.8 Hz)

To a solution of the resulting compound (2) (3.7 g) in diethylamine (25 ml), under an inert atmosphere, CuI (0.23 g) and $(Ph_3P)_2PdCl_2$ (0.438 g) were added and followed by addition of TMS-acetylene (2.3 ml) dropwise. The reaction mixture was stirred at room temperature for 4.5 hrs, then concentrated in vacuo. The concentrate was dissolved in ethyl acetate and satd. $NH_4Cl$ aq. The solution was stirred at room temperature for 15 min., then filtered through celite. The celite was washed with ethyl acetate. The filtrate was extracted with ethyl acetate and the organic layer was washed with satd. $NH_4Cl$ aq, water and brine. The organic layer was dried ($Na_2SO_4$), filtered, and concentrated in vacuo. The concentrate was purified by column chromatography on 150 g of silica gel and eluted with n-hexane-ethyl acetate (30:1). The TMS-ethynylphenyl ether derivative (3) was obtained as a pale yellow oil (2.29 g).

MASS (m/e): 266 (M+), 251 (BP), 215, 193, 175, 146, 115, 93, 77

IR (cm$^{-1}$, neat): 2944, 2146, 2062, 1602, 1503, 1467, 1284, 1245, 837

$^1$H-NMR (400 MHz, CDCl$_{13}$, ppm) d: 0.24 (9H, s), 2.23 (2H, m), 3.74 (2H, t, J=6.4 Hz), 4.11 (2H, t, J=6.0 Hz), 6.81 (2H, d, J=8.4 Hz), 7.40 (2H, d, J=9.2 Hz).

(b) 2-[3-(4-Ethynylphenoxy) propane-1-yl]2-azabicyclo [2.2.2]octane-3-one (Compound 5)

To a suspension of sodium hydride (NaH) (0.098 g) in DMF (2 ml), under an inert atmosphere, isoquinuclidine-3-one (4) (0.28 g) was added. The suspension was stirred at room temperature for 3 hrs. To the suspension, the solution of TMS-ethynylphenyl ether derivative (3) (0.3 g) in DMF (2 ml) and KI (0.009 g) were added, then the reaction mixture was stirred at 50° C. for 18 hrs. The reaction mixture was cooled to room temperature and poured into ice-water. The resulting solution was extracted with ethyl acetate and the organic layer was washed with water and brine. The organic layer was dried (Na$_2$SO$_4$), filtered, and concentrated in vacuo. The resulting precipitate was crystallized with ethyl ether. The resulting precipitate was collected by filtration, and was recrystallized with ethyl ether. Compound 5 was obtained as a pale yellow crystal (0.128 g).

MASS (m/e): 283 (M+), 262, 166 (BP), 138, 101, 81, 55

IR (cm$^{-1}$, KBr): 3190, 2938, 2860, 1647, 1605, 1503, 1476, 1458, 1287, 1248, 1173

$^1$H-NMR (400 MHz, CDCl$_3$, ppm) d: 1.60~1.86 (8H, m), 2.04 (2H, m), 2.58 (1H, bs), 2.99 (1H, s), 3.54 (3H, m), 3.99 (2H, t, J=6.4 Hz), 6.83 (2H, d, J=8.8 Hz), 7.41 (2H, d, J=8.8 Hz).

(c) 2-[3-(4-ethynylphenoxy)propane-1-yl]-2-azabicyclo [2.2.2]octane hydrochloride (Compound 10)

To a solution of TMS-ethynylphenyl ether derivative (3) (0.523 g) in DMF (4 ml), isoquinuclidine hydrochloride (8) (0.346 g), K$_2$CO$_3$ (0.68 g) and KI (0.006 g) were added, respectively. The reaction mixture was stirred at 50° C. for 18 hrs, then poured into ice-water. The resulting solution was extracted with ethyl acetate and the organic layer was washed with water and brine. The organic layer was dried (Na$_2$SO$_4$), filtered, and concentrated in vacuo. The resulting oil was purified by column chromatography on 25 g of alumina and eluted with chloroform. The product (compound 9) was obtained as yellow oil (0.238 g).

MASS (m/e): 269 (M+), 240, 124 (BP), 83,47

$^1$H-NMR (400 MHz, CDCl$_{13}$, ppm) d: 1.46~1.78 (7H, m), 1.92~2.20 (4H, m), 2.68 (1H, bs), 2.74 (2H, t, J=6.4 Hz), 2.81 (2H, bs), 2.99 (1H, s), 3.49 (1H, s), 4.04 (2H, t, J=6.4 Hz), 6.84 (2H, d, J=8.8 Hz), 7.41 (2H, d, J=8.8 Hz).

A solution of compound 9 (0.238 g) in ethyl acetate (2 ml) and methanol (4 ml), under cooling to a solution, was treated with HCl gas in ethyl ether dropwise to adjust the pH 5.0, then concentrated in vacuo. The concentrate was crystallized with ethyl acetate. The resulting precipitate was collected by filtration, and was recrystallized with ethyl acetate. Compound 10 was obtained as a pale yellow crystal(0.172 g).

MASS (m/e): 269 (M$^+$–HCl), 240, 124 (BP), 96, 75, 55

IR (cm$^{-1}$, KBr): 3154, 2944, 2866, 2632, 2554, 2500, 2090, 1605, 1506, 1485, 1287, 1248, 1179,843

$^1$H-NMR (400 MHz, DMSO-d6, ppm) d: 1.60~1.85 (6H, m), 2.01 (1H, s), 2.12~2.41 (4H, m), 3.02 (1H, d, J=12.0 Hz), 3.27 (1H, s), 3.30~3.42 (2H, m), 3.44 (2H, d, J=8.8 Hz), 3.53 (2H, bs), 4.21 (2H, m), 7.07 (2H, d, J=8.8 Hz), 7.53 (2H, d, J=8.8 Hz).

In this invention, all compounds as hydrochloride salt were prepared according to the method in example 1 (c).

Example 2

Ethyl 4-[3-(3-oxo-2-azabicyclo[2.2.2]octan-2-yl) propoxy]phenylpropiolate (Compound 6) and 4-[3-(3-oxo-2-azabicyclo[2.2.2]octan-2-yl)propoxy] phenylpropiolic acid (Compound 7)

To a solution of compound 5 (0.2 g), in example 1 (b), in THF (2 ml), n-BuLi in n-hexane solution (1.6 M) (0.9 ml) was added dropwise at −78° C. under the inert atmosphere, then was stirred for 0.5 hr. Then ethyl chloroformate (0.074 ml) was added to the reaction mixture and was stirred at 0° C. for 18 hrs. The reaction mixture was poured into satd. NH$_4$Cl aq and extracted with ethyl acetate.

The organic layer was washed with satd. NH$_4$Cl aq, water and brine. The organic layer was dried (Na$_2$SO$_4$), filtered, and concentrated in vacuo. The resulting oil was purified by column chromatography on 10 g of slica gel and eluted with n-hexane-ethyl acetate-methylene chloride (1:2:1). The product (compound 6) was obtained as a pale yellow oil (0.23 g).

MASS(m/e): 356 (M$^+$+1), 310, 228,201, 166, 138, 110, 81 (BP), 55

IR (cm$^{-1}$, neat): 2938, 2860, 2200, 1698, 1599, 1506, 1476, 1248, 1191, 834, 747

$^1$H-NMR (400 MHz, CDCl$_3$, ppm) d: 1.35 (3H, t, J=6.8 Hz), 1.60~1.95 (8H, m), 2.05 (2H, t, J=6.8 Hz), 2.59 (1H, s), 3.55 (3H, t+s, J=6.8 Hz), 4.02 (2H, t, J=6.4 Hz), 4.29 (2H, q, J=6.8 Hz), 6.87 (2H, d, J=8.8 Hz), 7.53 (2H, d, J=9.2 Hz).

To a solution of compound 6 (0.46 g) in ethanol (5 ml), 10% NaOH aq (0.55 ml) was added. The reaction mixture was refluxed for 5 hrs, then was concentrated in vacuo. The concentrate was treated with 10% HCl aq to adjust the pH 2.0, then was extracted with ethyl acetate and the organic layer was washed with water and brine. The organic layer was dried (Na$_2$SO$_4$), filtered, and concentrated in vacuo. The concentrate was crystallized with ethyl ether. The resulting precipitate was collected by filtration. Compound 7 was obtained as a pale yellow crystal (0.34 g).

MASS (m/e): 283 (M$^+$–44), 166 (BP), 138, 110, 81, 55

IR (cm$^-$, KBr): 2930, 2866, 2206, 1920, 1689, 1602, 1500, 1467, 1389, 1287, 1107, 1050, 948, 909, 831

$^1$H-NMR (400 MHz, DMSO-d6, ppm) d: 1.74 (8H, bs), 2.03 (2H, m), 2.44 (1H, s), 3.46 (OH, bs), 3.53 (2H, t, J=7.2 Hz), 3.74 (1H, s), 4.13 (2H, t, J=6.4 Hz), 7.12 (2H, d, J=8.4 Hz), 7.69 (2H, d, J=8.8 Hz).

Ethyl 4-[3-(2-azabicyclo[2.2 2]octan-2-yl)propoxy] phenylpropiolate (compound 11) was prepared from compound 10 according to the method of example 2, then compound 11 was treated with HCl in ethyl ether in accordance with the method of example 1 (c). Ethyl 4-[3-(2-azabicyclo[2.2.2]octan-2-yl) propoxy]phenylpropiolate hydrochloride (compound 12) was obtained as a pale yellow crystal. The physical data is shown as follows.

MASS (m/e): 341 (M$^+$–HCl), 312, 152, 124 (BP), 96, 55

IR (cm$^{-1}$ , KBr :2932, 2860, 2632, 2560, 2494, 2200, 1704, 1602, 1509, 1284, 1251, 1191, 1161, 834.

Compound 13 and 14 were prepared in accordance with the method of example 1 (a) and 1 (b) using either 1, 2-dibromoethane or 1, 4-dibromobutane in the place of 1-bromo-3-chloropropane which was used in the method of example 1 (a). Their physical data are shown as follows.

The physical data of 2-[2-(4-ethynylphenoxy)ethyl]-2-azabicyclo[2.2.2octane-one (compound 13).

MASS (m/e): 269 (M+), 152 (BP), 118, 81, 55

IR (cm$^{-1}$, KBr):2938, 1656, 1605, 1506, 1479, 1458, 1287, 1239, 1173, 1059, 831

$^1$H-NMR (400 MHz, CDCl$_{13}$, ppm) d: 1.59~1.90 (8H, m), 2.57 (1H, s), 3.00 (1H, s), 3.73 (11H, s), 3.76 (2H, t, J=5.2 Hz), 4.10 (2H, t, J=5.2 Hz), 6.81 (2H, d, J=8.4 Hz), 7.42 (2H, d, J=8.8 Hz).

The physical data of 2-[4-(4-ethynylphenoxy)butane-1-yl]-2-azabicyclo[2.2.2]-octane-3-one (compound 14).

MASS (m/e): 297 (M+), 180 (BP), 138, 118, 101, 81, 55

IR (cm$^{-1}$, KBr) :3196, 2932, 1653, 1611, 1509, 1479, 1458, 1434, 1290, 1257, 1173, 828

$^1$H-NMR (400 MHz, CDCl$_3$, ppm) d: 1.50~1.85 (12H, m), 2.58 (1H, s), 2.99 (1H, s), 3.43 (2H, t, J=7.2 Hz), 3.56 (1H, s), 3.99 (2H, t, J=6.4 Hz), 6.82 (2H, d, J=d, J=8.8 Hz).

Example 3

Ethyl 4-[4-[3-(3-oxo-2-azabicyclo[2.2.2]octan-2-yl)propoxy]phenylethynyl]-benzoate (Compound 15) and 4-[4-[3-(3-oxo-2-azabicyclo[2.2.2]octan-2-yl)propoxy]phenylethynyl]1-benzoic acid (Compound 16)

To a solution of compound 5 (0.5 g) in acetonitrile (30 ml), ethyl 4-iodobenzoate (0.49 g) was added, then triethylamine (3.5 ml), Me$_3$N(Bn)Cl (0.013 g) and Pd(PPh$_3$)$_4$ (0.041 g) were added, respectively. The reaction mixture was stirred at 130° C. in a sealed tube for 18 hrs. The reaction mixture was cooled to room temperature, then was poured into satd. NH$_4$Cl aq and ethyl acetate. The resulting suspension was stirred at room temperature for 15 min., then was filtered through celite. The celite was washed with ethyl acetate. The filtrate was extracted with ethyl acetate. The organic layer was washed with satd. NH$_4$Cl aq, water and brine. The organic layer was dried (Na$_2$SO$_4$), filtered, and concentrated in vacuo. The resulting oil was purified by column chromatography on 35 g of slica gel and eluted with n-hexane-ethyl acetate (1: 4). The product (compound 15) was obtained as a pale yellow crystal (0.54 g).

MASS (m/e): 431 (M+), 386, 265, 221, 192 (BP), 166, 138, 110

IR (cm$^{-1}$, KBr): 3418, 2914, 1710, 1671, 1599, 1269

$^1$H-NMR (400 MHz, CDCl$_{13}$, ppm) d: 1.40 (3H, t, J=7.3 Hz), 1.65~1.79 (8H, m), 2.05 (2H, m), 2.58 (1H, m), 3.54~3.58 (3H, m), 4.02 (2H, t, J=6.4 Hz), 4.38 (2H, q, J=7.3 Hz 6.88 (2H, d, J=8.3 Hz), 7.47 (2H, d, J=8.3 Hz) 7.56 (2H, d, J=8.3 Hz), 8.01 (2H, d, J=8.3 Hz).

4-[4-[3-(3-oxo-2-azabicyclo[2.2.2]octan-2-yl) propoxy]phenylethynyl]-benzoic acid (compound 16) was prepared from compound 15 in accordance with the synthetic route from compound 6 to compound 7 in example 2. The physical data of compound 16 are shown as follows.

MASS (m/e): 238 (M$^{30}$–166), 193, 166 (BP), 138, 110, 73, 55

IR (cm$^{-1}$, KBr) :3400, 2944, 2872, 2212, 1716, 1686, 1632, 1602, 1491, 1467, 1407, 1383, 1341, 1311, 1284, 1251, 1230, 1173, 1140, 1104, 1050, 945, 858, 834, 771

$^1$H-NMR (400 MHz, DMSO-d6, ppm) d: 1.75 (8H, bs), 2.03 (2H, m), 2.45 (1H, s), 3.54 (2H, t, J=7.2 Hz), 3.75 (1H, s), 4.12 (2H, t, J=6.4 Hz), 7.10 (2H, d, J=8.8 Hz), 7.64 (2H, d, J=8.8 Hz), 7.74 (2H, d, J=8.4 Hz), 8.07 (2H, d, J=8.8 Hz).

(a) Compound 19 and 20 were prepared in accordance with the method of example 3 using compound 9 in the place of compound 5 which used in the method of example 3. These physical data are shown as follows.

The physical data of 4-[4-[3-(2-azabicyclo[2.2.2]octan-2-yl)propoxy]phenylethynyl]-benzoic acid hydrochloride (compound 19)

MASS (m/e): 252, 221, 124, 66 (BP)

IR (cm$^{31\ 1}$, KBr): 3400, 2944, 2572, 2212, 1707, 1599, 1473, 1434, 1407, 1284, 1248, 1179, 1098, 963, 858

$^1$H-NMR (400 MHz, DMSO-d6, ppm) d: 1.65~1.90 (6H, m), 2.01 (1H, bs), 2.15~2.40 (4H, m), 3.07 (1H, bs), 3.54 (2H, m), 3.99 (2H, s), 4.23 (2H, bs), 7.14 (2H, d J=8.8 Hz 7.67 (2H, d, J=8.8 Hz), 7.77 (2H, d, J=8.0 Hz), 8.10 (2H, d, J=8.8 Hz)

The physical data of Ethyl 4-[4-[3-(2-azabicyclo[2.2.2]octan-2-yl)propoxy]phenylethynyl]-benzoate hydrochloride (compound 20).

MASS (m/e): 417 (M+–HCl), 278, 153, 124, 83

IR (cm$^{-1}$,KBr):3418, 2920, 1713, 1599, 1269, 1248

$^1$H-NMR (400 MHz, DMSO-d6, ppm) d: 1.41 (3H, t, J=6.8 Hz), 1.65~2.67 (1H, m), 3.17~3.22 (5H, m), 4.06 (2H, t, J=5.9 Hz), 4.38 (2H, q, J=6.8 Hz), 6.86 (2H, d J=8.8 Hz), 7.47 (2H, d, J=8.8 Hz), 7.56 (2H, d, J=8.3 Hz), 8.01 (2H, d, J=8.8 Hz).

(b) Compound 21 was prepared in accordance with the method of example 3 using ethyl 5-bromo-thiophene-2-carboxylate in the place of ethyl 4-iodobenzoate which used in the method of example 3. The physical data are shown as follows.

The physical data of 5-[4-[3-(3-oxo-2-azabicyclo[2.2.2]octan-2-yl)propoxy]phenylethynyl]-thiophene-2-carboxylic acid (compound 21).

MASS (m/e): 366 (M+–43), 307, 200, 166 (BP), 138, 110, 81, 55

IR (cm$^{-1}$, KBr):3400, 2944, 2866, 2620, 2200, 1692, 1626, 1506, 1452, 1395, 1290, 1254, 1173, 1140, 1053, 1023, 825

$^1$H-NMR (400 MHz, DMSO-d6, ppm) d: 1.75 (8H, bs), 2.03 (2H, m), 2.45 (1H, s), 3.54 (2H, t, J=6.8 Hz), 3.74 (1H, s), 4.12 (2H, t, J=6.4 Hz), 7.12 (2H, d, J=8.8 Hz), 7.50 (1H d, J=3.6 Hz), 7.64 (2H, d, J=9.2 Hz), 7.78 (1H, d, J=3.6 Hz).

(c) Compounds 22, 23, and 24 were prepared in accordance with the method of example 3 using 4-(quinolin-5-yl)phenyl triflate (compound 30) or 4-(isoquinuclidin-3-one-2-yl) phenyl triflate (compound 33) in the place of ethyl 4-iodobenzoate which was used in the method of example 3. On the other hand, compound 25 was prepared in accordance with the method of example 3 using compound 9 in the place of compound 5 which used in the method of example 3, and using 5-iodo-quinoline in the place of ethyl 4-iodobenzoate which was used in the method of example 3. The physical data for compounds 22, 23, 24 and 25 are shown as follows.

The physical data of 2-[3-[4-(quinolin-5-yl-ethynyl) phenoxy]propan-1-yl]-2-azabicyclo[2.2.2]-octan-3-one hydrochloride (compound 22).

MASS (m/e): 411 (M$^+$–HCl), 271, 245, 216, 166 (BP), 138, 110, 81, 55

IR (cm$^{-1}$, KBr): 3364, 2932, 2860, 2476, 2200, 1656, 1602, 1584, 1509, 1251 hu 1H-NMR (400 MHz, CD$_3$OD, ppm) d: 1.75~1.90 (8H, m), 2.11 (2H, m), 2.54 (1H, s), 3.64 (2H, t, J=6.8 Hz), 3.78 (1H, s), 4.12 (2H, t, J=6.4 Hz), 7.08 (2H, d, J=8.8 Hz), 7.70 (2H, d, J=8.8 Hz), 8.15~8.26 (4H, m), 9.30 (1H, dd, J=5.2, 2.0 Hz), 9.58 (1H, d, J=8.4 Hz).

The physical data of 2-[3-[4-(4-(quinolin-5-yl) phenylethynyl]phenoxy]propan-1-yl]-2-azabicyclo[2.2.2] octan-3-one hydrochloride (compound 23).

MASS(m/e): 321 (M$^+$–HCl–166), 166 (BP), 138, 110, 81, 55

IR (cm$^{-1}$, KBr): 1638, 1599, 1245

$^1$H-NMR (400 MHz, CDCl$_3$, ppm) d: 1.60~1.90 (8H, m), 2.06 (2H, m), 2.59 (1H, s), 3.56 (3H, t+s, J=6.8 Hz), 4.02 (2H, t, J=6.4 Hz), 6.89 (2H, d, J=8.8 Hz), 7.37 (1H, dd, J=8.8, 4.4 Hz), 7.44 (2H, d, J=8.4 Hz), 7.51 (3H, m), 7.64 (2H, d, J=8.0 Hz), 7.76 (1H, dd, J=8.8, 6.8 Hz), 8.14 (1H, d, J=8.0 Hz), 8.24 (1H, d, J=8.8 Hz), 8.94 (1H, d, J=9.4 Hz).

The physical data of 2-[3-[4-[4-(3-oxo-2-azabicyclo [2.2.2]octan-2-yl)phenylethynyl]phenoxy]propan-1-yl]-2-azabicyclo[2.2.2]octan-3-one (compound 24).

MASS (m/e): 350 (M$^{30}$–132), 262, 216, 183, 152, 115, 83 (BP), 47

IR (cm$^{-1}$, KBr): 2932, 1665, 1605, 1512, 1470, 1455, 1419, 1401, 1278, 1245, 1170, 828

$^1$H-NMR (400MHz, CDCl$_3$, ppm) d: 1.60~2.10 (18H, m), 2.58 (1H, s), 2.74 (1H, s), 3.55 (3H, t+s, J=7.2 Hz), 4.01 (2H, t, J=6.4 Hz), 4.15 (1H, s), 6.86 (2H, d, J=8.8 Hz), 7.33 (2H, d, J=8.8 Hz), 7.45 (2H, d, J=8.8 Hz), 7.49 (2H, d, J=8.8 Hz).

The physical data of 2-[3-[4-(quinolin-5-yl-ethynyl) phenoxy]propan-1-yl]-2-azabicyclo[2.2.2]octane dihydrochloride (compound 25).

MASS (m/e): 397 (M$^-$2HCl), 245, 216, 152, 124 (BP), 96, 55

IR (cm$^{-1}$, KBr): 3406, 2938, 2860, 2686, 2200, 1587, 1509, 1248

$^1$H-NMR (400 MHz, CD$_3$OD, ppm) d: 1.70~2.01 (6H, m), 2.05 (1H, s), 2.10~2.40 (4H, m), 3.14 (1H, d, J=12.4 Hz), 3.40~3.53 (1H, m), 3.55 (1H, s), 3.63 (1H, d, J=12.4 Hz), 4.20~4.30 (2H, m), 7.11 (2H, d, J=8.8 Hz), 7.74 (2H, d, J=8.8 Hz), 8.16~8.31 (4H, m), 9.31 (1H, d, J=6.4 Hz), 9.58 (1H, d, J=8.4 Hz).

Example 4

4-(quinolin-5-yl)phenyltriflate (Compound 30) and 4-(isoquinuclidin-3-one-2-yl)phenyl triflate (Compound 33)

(a) 4-(quinolin-5-yl) phenyltriflate (Compound 30)

To a solution of 4-iodoanisole (26) (5 g) in THF (45 ml), n-BuLi in n-hexane solution (1.6 M) (16.02 ml) was added at –78° C. under the inert atmosphere. The reaction mixture was stirred at –78° C. for 1 hr, then a tri (i-propyl) borate (5.9 ml) was added. The reaction mixture was stiffed at room temperature for 2 hrs. The reaction mixture was cooled to room temperature and poured into satd. NH$_4$Cl aq. The resulting solution was added with ethyl acetate and was stirred at room temperature for 1.5 hrs. The reaction mixture was extracted with ethyl acetate and then the organic layer was washed with satd. NH$_4$Cl aq, water and brine. The organic layer was dried (Na$_2$SO$_4$), filtered, and concentrated in vacuo. The concentrate was crystallized with n-hexane-ether (4:1). The resulting precipitate was collected by filtration. 4-methoxyphenylboronic acid (27) was obtained as a white crystal (1.98 g).

To a solution of 4-methoxyphenylboronic acid (27) (1.64 g) and 5-iodoquinoline (2.5 g) in toluene (20 ml), 2M sodium bicarbonate (Na$_2$CO$_3$)aq (20 ml) and Pd(PPh$_3$)$_4$ (1.13 g) were added, respectively. The mixture was refluxed for 21 hrs and poured into ice-water. The solution was extracted with ethyl acetate, then the organic layer was washed with satd. NH$_4$Cl aq, water and brine. The organic layer was dried (Na$_2$SO$_4$), filtered, and concentrated in vacuo. The resulting oil was purified by column chromatography on 120 g of silica gel and eluted with chloroform-methanol (100:1). The product (compound 28) was obtained as a red crystal (1.65 g).

MASS (m/e): 235 (M$^+$, BP), 191, 165, 139, 118, 88, 63

IR (cm$^{-1}$, KBr): 3022, 2944, 1608, 1569, 1506, 1461, 1389, 1287, 1242, 1173, 1029, 960, 801

$^1$H-NMR (400 MHz, CDCl$_3$, ppm) d: 3.90 (3H, s), 7.05 (2H, d, J=8.8 Hz), 7.35 (1H, dd, J=8.8, 4.4 Hz), 7.39 (2H, d, J=8.8 Hz), 7.49 (1H, d, J=7.2 Hz), 7.74 (1H, dd, J=8.8, 7.2 Hz), 8.10 (1H, d, J=8.4 Hz), 8.26 (1H, d, J=8.4 Hz), 8.92 (1H, dd, J=4.4, 2.0 Hz).

To a solution of 5-(4-methoxyphenyl)quinoline (compound 28) (1.08 g) in methylene chloride (10 ml), a solution of boron tribromide in methylene chloride (1.0 M) (5.5 ml) was added at –40° C. under the inert atmosphere. The reaction mixture was stirred at room temperature for 15 hrs, then it was poured into a cooled solution of sodium hydrocarbonate (NaHCO$_3$). The solution was extracted with ethyl acetate and then the organic layer was washed with satd. NH$_4$Cl aq, water and brine. The organic layer was dried (Na$_2$SO$_4$), filtered, and concentrated in vacuo. The concentrate was crystallized with ethyl ether-methanol (10:1). The resulting precipitate was collected by filtration. 4-(quinoline-5-yl)phenol (29) was obtained as a yellow crystal (0.82 g).

$^1$H-NMR (400 MHz, CD$_3$OD, ppm) d:7.05 (2H, d, J=8.8 Hz), 7.40 (2H, d, J=8.4 Hz), 7.95 (1H, t, J=4.0 Hz), 8.09 (1H, dd, J=8.4, 5.6 Hz), 8.25 (2H, d, J=4.4 Hz), 9.19 (1H, d J=8.4 Hz), 9.24 (1H, dd, J=5.6, 1.6 Hz).

To a suspension of 4-(quinoline-5-yl)phenol (29) (0.2 g) in methylene chloride (2 ml), pyridine (0.08 ml) and tri-fluromethane sulfonic acid anhydride (0.3 ml) were added, respectively. The reaction mixture was stirred at 0° C. for 1 hr under the inert atmosphere, then was poured into ice-satd. NH$_4$Cl aq. The solution was extracted with ethyl acetate and then the organic layer was washed with satd. NH$_4$Cl aq, water and brine. The organic layer was dried (Na$_2$SO$_4$), filtered, and concentrated in vacuo. The product (4-(quinolin-5-yl)phenyltriflate (compound 30)) was obtained as a yellow oil (0.21 g). The product (Compound 30) was used without further purification.

MASS (m/e): 353 (M⁺), 255, 220 (BP), 191, 165, 128, 69, 49.

(b) 4-(Isoquinuclidin-3-one-2-yl)phenyltriflate (compound 33)

A mixture of isoquinuclidin-3-one (compound 4) (4.4 g), 4-iodoanisole (compound 26) (10 g), CuI (1.34 g) and K₂CO₃ (5.1 g) were stirred at 150° C. for 7 hrs. The reaction mixture was cooled to room temperature and then was poured into ethyl acetate and satd. NH₄Cl aq. The suspension was stirred for 15 min, then filtered to celite. The filtrate was extracted with ethyl acetate and then the organic layer was washed with satd. NH₄Cl aq, water and brine. The organic layer was dried (Na₂SO₄), filtered, and concentrated in vacuo. The concentrate was purified by column chromatography on 200 g of silica gel and eluted with chloroform-methanol (100:1). The product (4-(isoquinuclidin-3-one-2-yl) anisole (31)) was obtained as a white crystal (7.1 g).

MASS (m/e): 231 (M⁺, BP), 202, 175, 134, 77, 55

¹H-NMR (400 MHz, CDCl₃, ppm) d: 1.70~1.90 (4H, m), 1.98 (4H, d, J=7.2 Hz), 2.72 (1H, s), 3.80 (3H, s), 3.99 (1H, s), 6.88 (2H, d, J=8.4 Hz), 7.23 (2H, d, J=9.2 Hz).

4-(Isoquinuclidin-3-one-2-yl) phenyl triflate (compound 33) was prepared from compound 31 in accordance with the method of example 4 (b). The physical data of compound 33 are shown as follows.

MASS (m/e): 349 (M⁺), 277, 216, 188, 160, 134, 108, 81 (BP), 53

¹H-NMR (400 MHz, CDCl₃, ppm) d: 1.76~2.08 (8H, m), 2.75 (1H, s), 4.15 (1H, s), 7.26 (2H, d, J=9.2 Hz), 7.45 (2H, d, J=9.2 Hz).

Example 5

2-[3-[(2- Allyl-4-ethynyl)phenoxy]propane-1-yl]-2-azabicyclo[2.2.2]octan-3-one (Compound 37) and 2-[3-[(2-allyl-4-ethynyl)phenoxy]propane-1-yl]-2-azabicyclo[2.2.2]octane hydrochloride (Compound 38)

(a) Preparation of 2-allyl-4-bromophenol (Compound 36)

To a solution of 4-bromophenol (34) (20 g) in acetone (100 ml), allyl bromide (11 ml) and K₂CO₃ (24 g) were added, respectively. The reaction mixture was refluxed for 2 hrs, then was concentrated in vacuo. The concentrate was poured into ice-water and then was extracted with ethyl acetate. The organic layer was washed with water and brine. The organic layer was dried (Na₂SO₄), filtered, and concentrated in vacuo. The concentrate was distilled under reduced pressure. The product (compound 35) was obtained as a white oil. (bp₁₄:124~127° C.).

MASS (m/e): 214 (M⁺+2), 212 (M⁺), 174, 172, 145, 143, 133, 119, 117, 105, 84, 63 (BP)

IR (cm⁻¹, neat): 3070, 2860, 1578, 1485, 1284, 1236, 996, 816, 597, 501

¹H-NMR (400 MHz, CDCl₃,ppm) d: 4.50 (2H, dt, J=5.4, 1.5 Hz), 5.29 (1H, dd, J=10.3, 1.5 Hz), 5.40 (1H, dq, J=17.6, 1.5 Hz), 5.99~6.07 (1H, m), 6.79 (2H, d, J=9.3 Hz), 7.36 (2H, d, J=9.3 Hz).

Compound 35 (10 g) was refluxed in the flask for 10 min under the inert atmosphere, then was cooled to room temperature and then was dissolved in ether. The solution was extracted with 20% NaOH aq, then the water solution was treated with conc. HCl to adjust the pH 3.0, extracted with ether and the organic layer was washed with water and brine. The organic layer was dried (Na₂SO₄ ), filtered, and concentrated in vacuo. The concentrate was distilled under reduced pressure. The product (Compound 36) was obtained as a white oil. (bp₁₆:145~149° C.).

MASS (m/e): 214 (M⁺+2), 212 (M⁺), 199, 197, 187, 185, 133, 105, 77, 51 (BP)

IR (cm⁻¹, neat): 3436, 3070, 2968, 2896, 1482, 1410, 1260, 1206, 1161, 1004, 918, 807, 627

¹H-NMR (400 MHz, CDCl₃, ppm) d: 2.21 (2H, m), 3.36 (2H, d, J=6.4 Hz), 5.13~5.19 (2H, m), 5.92~6.02 (1H, m), 6.69 (1H, d, J=8.8 Hz).

(b) Preparation of 2-[3-[(2-allyl-4-ethynyl)phenoxy]propane-1-yl]-2-azabicyclo[2.2.2]octan-3-one (Compound 37) and 2-[3-(2-allyl-4-ethynyl)phenoxy]propane-1-yl]-2-azabicyclo[2.2.2]octane hydrochloride (Compound 38)

2-[3-[(2-Allyl-4-ethynyl)phenoxy]propane-1-yl]-2-azabicyclo[2.2.2]octan-3-one (compound 37) was prepared in accordance with example 1 (a) and I (b) using compound 36. The physical data was shown as follows.

MASS (m/e): 323 (M⁺), 166 (BP), 138, 110, 81

IR (cm⁻¹, neat): 3286, 3202, 2938, 2860, 2098, 1656, 1479, 1245, 750

⁻¹H-NMR (400 MHz, CDCl₃, ppm) d: 1.61~1.81 (8H, m), 1.90 (2H, dd, J=6.4, 1.5 Hz), 2.07 (2H, m), 2.58 (1H, m), 2.99 (1H, s), 3.54~3.58 (3H, m), 4.02 (2H, t, J=6.4 Hz), 6.24 (1H, m), 6.64 (2H, m), 6.77 (1H, m), 7.28~7.54 (2H, m).

2-[3-[(2-Allyl-4-ethynyl)phenoxy]propane-1-yl]-2-azabicyclo[2.2.2]octane hydrochloride (compound 38) was prepared in accordance with example 1(a) and 1(c) using compound 36. The physical data was shown as follows.

MASS (m/e): 309 (M⁺–HCl), 150, 124 (BP), 96, 69

IR (cm⁻¹, KBr): 3418, 3160, 2938, 2572, 1605, 1497, 1248, 1119, 804

¹H-NMR (400 MHz, CDCl3, ppm) d: 1.71~2.02 (8H, m), 2.44~2.78 (4H, m), 3.00 (1H, s), 3.20~3.35 (5H, m), 3.85 (1H, m), 4.10 (2H, m), 4.98~5.07 (2H, m), 5.92 (1H, m) 6.76 (1H, m), 7.28~7.37 (2H, m).

What is claimed is:

1. A compound of formula (I) or hydrochloride salt thereof,

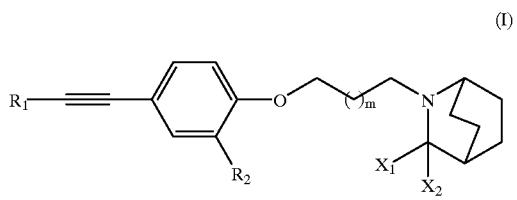

wherein:
R₁ is hydrogen atom, carboxyl group, ethoxycarbonyl group, 4-(ethoxycarbonyl)phenyl group, 4-(carboxy) phenyl group, 2-(carboxy)-thiophene-5-yl group, quinoline-5-yl group, 4-(quinoline-5-yl)phenyl group or 4-(3-oxo-2-azabicyclo[2.2.2]octane-2-yl)-phenyl group;

R₂ is hydrogen atom or allyl group;

both X₁ and X₂ are hydrogen atom or X₁ and X₂ form an oxo group;

m stands for an integer of 0 to 2.

2. A method for preparation of a compound of formula (I) or hydrochloride salt thereof, as set forth in claim 1, comprising reacting a compound of formula (II),

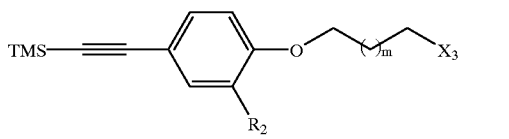
(II)

wherein:
- $R_2$ and m are defined above;
- $X_3$ is bromine atom or chlorine atom;
- TMS represents trimethylsilyl group, with a compound of formula (III) or hydrochloride salt thereof,

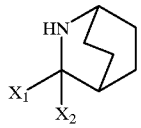
(III)

wherein: both $X_1$ and $X_2$ are defined above.

3. A method for preparation of a compound of formula (I) or hydrochloride salt thereof, as set forth in claim 1, comprising reacting a compound of formula (IV),

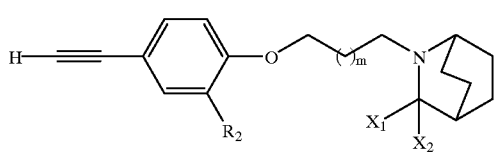
(IV)

wherein:
- $R_2$, $X_1$, $X_2$ and m are defined above, with a compound of formula (V), $R_1$-$X_4$ (V)

wherein:
- $R_1$ is defined above; and
- $X_4$ is halogen atom or triflate group.

4. A compound according to claim 1 or hydrochloride salt thereof, wherein $R_1$ is a hydrogen atom.

5. A compound according to claim 1 or hydrochloride salt thereof, wherein $R_1$ is a carboxyl group.

6. A compound according to claim 1 or hydrochloride salt thereof, wherein $R_1$ is an ethoxycarbonyl group.

7. A compound according to claim 1 or hydrochloride salt thereof, wherein $R_1$ is a 4-(ethoxycarbonyl)-phenyl group.

8. A compound according to claim 1 or hydrochloride salt thereof, wherein $R_1$ is a 4-(carboxy)phenyl group.

9. A compound according to claim 1 or hydrochloride salt thereof, wherein $R_1$ is a 2-(carboxy)-thiophene-5-yl group.

10. A compound according to claim 1 or hydrochloride salt thereof, wherein $R_1$ is a quinoline-5-yl group.

11. A compound according to claim 1 or hydrochloride salt thereof, wherein $R_1$ is a 4-(quinoline-5-yl)-phenyl group.

12. A compound according to claim 1 or hydrochloride salt thereof, wherein $R_1$ is a 4-(3-oxo-2-azabicyclo[2.2.2]octane-2-yl)-phenyl group.

13. A compound according to claim 1 or hydrochloride salt thereof, wherein $R_2$ is a hydrogen atom.

14. A compound according to claim 1 or hydrochloride salt thereof, wherein $R_2$ is an allyl group.

15. A compound according to claim 1 or hydrochloride salt thereof, wherein $X_1$ and $X_2$ are both hydrogen atoms.

16. A compound according to claim 1 or hydrochloride salt thereof, wherein $X_1$ and $X_2$ together form an oxo group.

17. A compound according to claim 1 or hydrochloride salt thereof, wherein m is 0.

18. A compound according to claim 1 or hydrochloride salt thereof, wherein m is 1.

19. A compound according to claim 1 or hydrochloride salt thereof, wherein m is 2.

* * * * *